(12) United States Patent
del Rio et al.

(10) Patent No.: US 12,108,958 B2
(45) Date of Patent: *Oct. 8, 2024

(54) DISPOSABLE BURR ATTACHMENT

(71) Applicant: DePuy Synthes Products, Inc., Raynham, MA (US)

(72) Inventors: Eddy H. del Rio, Royal Palm Beach, FL (US); Douglas A. Perry, Palm Beach Gardens, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 110 days.

This patent is subject to a terminal disclaimer.

(21) Appl. No.: 17/101,314

(22) Filed: Nov. 23, 2020

(65) Prior Publication Data

US 2021/0068849 A1    Mar. 11, 2021

Related U.S. Application Data

(63) Continuation of application No. 15/911,796, filed on Mar. 5, 2018, now Pat. No. 10,842,508, which is a continuation of application No. 14/490,079, filed on Sep. 18, 2014, now Pat. No. 9,907,559, which is a continuation of application No. 12/387,828, filed on May 8, 2009, now Pat. No. 8,870,873.

(51) Int. Cl.
*A61B 17/16* (2006.01)

(52) U.S. Cl.
CPC ...... *A61B 17/1631* (2013.01); *A61B 17/1617* (2013.01); *A61B 17/162* (2013.01); *A61B 17/1679* (2013.01); *A61B 17/1688* (2013.01)

(58) Field of Classification Search
CPC ............ A61B 17/1615; A61B 17/1617; A61B 17/162; A61B 17/1631; A61B 17/1633; A61B 17/1642; A61B 17/1662; A61B 17/1679; A61B 17/1688; B23B 45/005
USPC ....................................................... 408/127
See application file for complete search history.

(56) References Cited

U.S. PATENT DOCUMENTS

| | | | |
|---|---|---|---|
| 1,630,239 A | 5/1927 | Binkley et al. | |
| 2,725,495 A | 11/1955 | Rively | |
| 3,867,943 A | 2/1975 | Nordin | |
| 4,098,292 A | 7/1978 | Evans | |
| 4,234,277 A | 11/1980 | Benson et al. | |
| 4,265,231 A * | 5/1981 | Scheller, Jr. ..... | A61B 17/32002 606/103 |
| 4,541,423 A | 9/1985 | Barber | |

(Continued)

OTHER PUBLICATIONS

U.S. Official Action, dated Dec. 14, 2012, received in connection with related U.S. Appl. No. 12/387,828.

(Continued)

*Primary Examiner* — Amy R Sipp
(74) *Attorney, Agent, or Firm* — BakerHostetler

(57) ABSTRACT

A burr attachment designed for use with a curved burr attachment or other chuck attachments that includes a tube with a wire shaft supported therein and a coil spring surrounding said wire shaft and having each of the coils touch the outer periphery surface of the wire shaft and the inner peripheral surface of said tube to enhance cooling of said outer periphery of said tube from the heat generated by said wire shaft and attenuate vibrations while allowing said burr attachment to be bent without kinking.

19 Claims, 4 Drawing Sheets

(56) References Cited

U.S. PATENT DOCUMENTS

| | | |
|---|---|---|
| 4,686,982 A | 8/1987 | Nash |
| 4,728,231 A | 3/1988 | Kunimori et al. |
| 4,811,736 A | 3/1989 | Griggs et al. |
| 4,842,578 A * | 6/1989 | Johnson ............ A61B 17/1675 |
| | | 606/85 |
| 5,242,461 A * | 9/1993 | Kortenbach ... A61B 17/320725 |
| | | 606/159 |
| 5,271,697 A | 12/1993 | Johnson et al. |
| 5,273,052 A * | 12/1993 | Kraus ................ A61M 25/104 |
| | | 600/585 |
| 5,330,480 A | 7/1994 | Meloul et al. |
| 5,358,509 A | 10/1994 | Fine et al. |
| 5,437,630 A * | 8/1995 | Daniel ............ A61B 17/32002 |
| | | 606/180 |
| 5,478,093 A | 12/1995 | Eibl et al. |
| 5,499,984 A | 3/1996 | Steiner et al. |
| 5,505,737 A | 4/1996 | Gosselin et al. |
| 5,507,769 A | 4/1996 | Marin et al. |
| 5,741,263 A | 4/1998 | Umber et al. |
| 5,766,190 A * | 6/1998 | Wulfman ............ A61B 17/1617 |
| | | 606/159 |
| 5,928,241 A | 1/1999 | Menut et al. |
| 5,895,179 A | 4/1999 | Gschwend et al. |
| 6,267,679 B1 * | 7/2001 | Romano ................ F16C 1/02 |
| | | 175/320 |
| 6,287,114 B1 | 9/2001 | Meller et al. |
| 7,066,940 B2 | 6/2006 | Riedel et al. |
| 7,488,322 B2 | 2/2009 | Brunnett et al. |
| 7,604,636 B1 | 10/2009 | Walters et al. |
| 8,273,097 B2 | 9/2012 | Malla et al. |
| 8,608,766 B2 | 12/2013 | Malla et al. |
| 8,870,873 B2 | 10/2014 | Del Rio et al. |
| 8,939,979 B2 | 1/2015 | Del Rio et al. |
| 2002/0009341 A1 * | 1/2002 | Vasudeva ............ B23B 31/005 |
| | | 408/226 |
| 2002/0038129 A1 | 3/2002 | Peters et al. |
| 2002/0071728 A1 | 6/2002 | Keefe et al. |
| 2002/0151902 A1 | 10/2002 | Riedel et al. |
| 2004/0194790 A1 | 10/2004 | Laufer et al. |
| 2005/0177168 A1 * | 8/2005 | Brunnett ............ A61B 17/1624 |
| | | 606/80 |
| 2006/0229624 A1 | 10/2006 | May et al. |
| 2006/0241630 A1 * | 10/2006 | Brunnett ............ A61B 17/1624 |
| | | 606/80 |
| 2007/0088354 A1 * | 4/2007 | Sugita ................ A61B 18/1492 |
| | | 606/45 |
| 2007/0100334 A1 * | 5/2007 | McFarlin ............ A61B 17/1622 |
| | | 606/45 |
| 2007/0100336 A1 | 5/2007 | McFarlin et al. |
| 2007/0264093 A1 * | 11/2007 | White .................. B23B 45/005 |
| | | 408/127 |
| 2008/0249481 A1 * | 10/2008 | Crainich ............ A61B 17/8805 |
| | | 606/80 |
| 2008/0306334 A1 | 12/2008 | Okada |
| 2009/0131940 A1 | 5/2009 | Brunnett et al. |
| 2010/0063524 A1 | 3/2010 | McCombs |

OTHER PUBLICATIONS

U.S. Official Action, dated Jan. 19, 2012, received in connection with related U.S. Appl. No. 12/387,828.

* cited by examiner

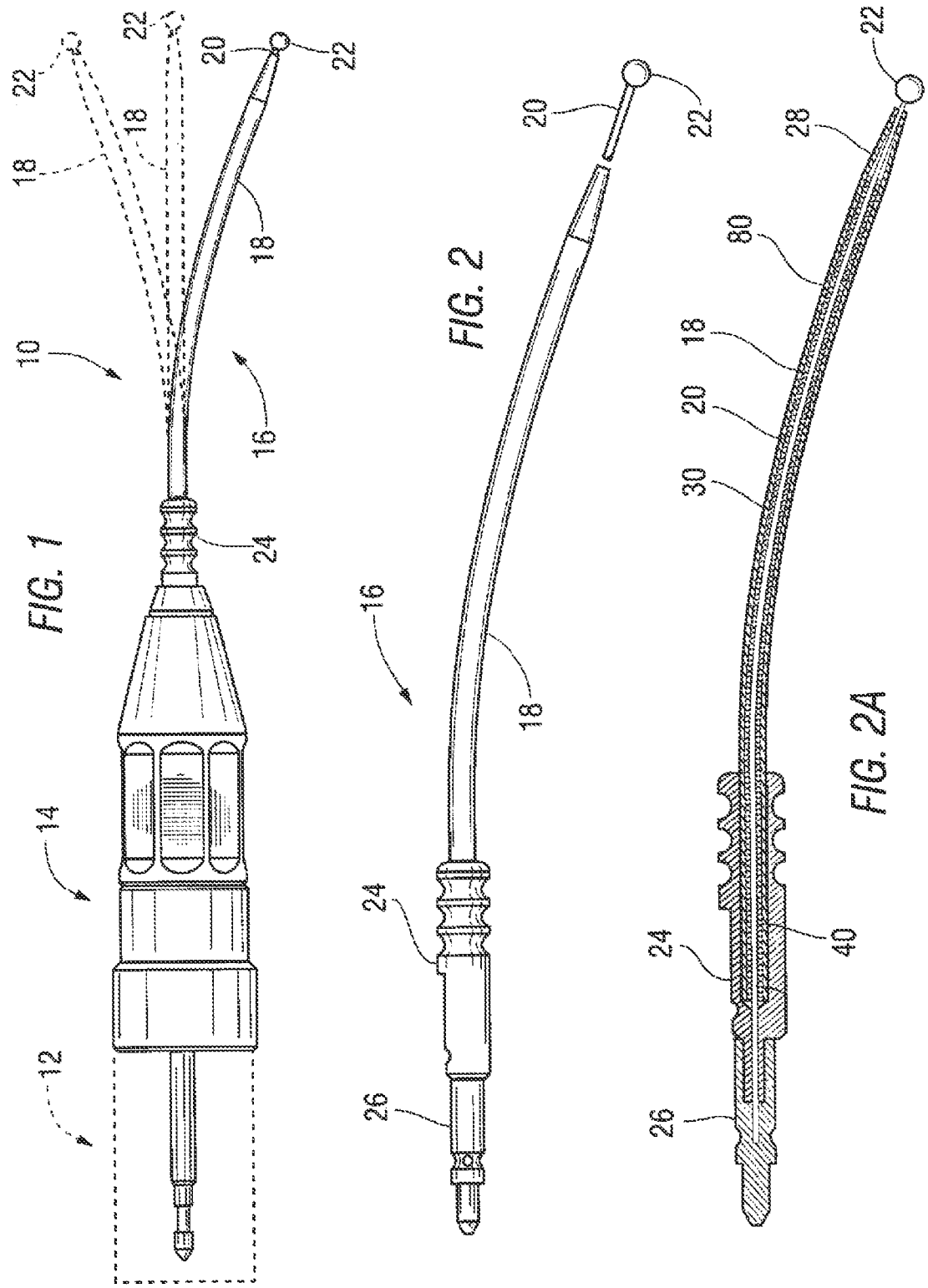

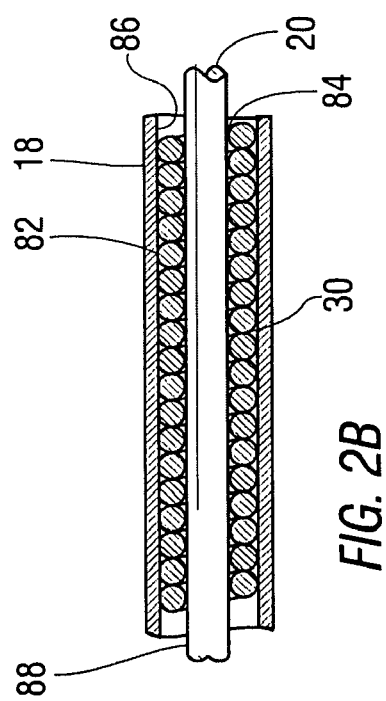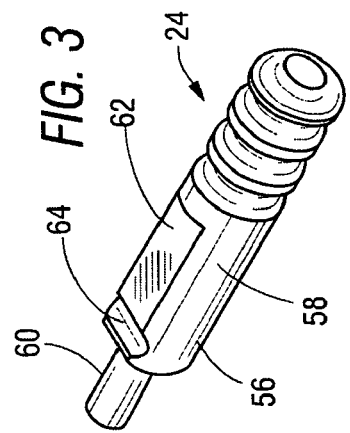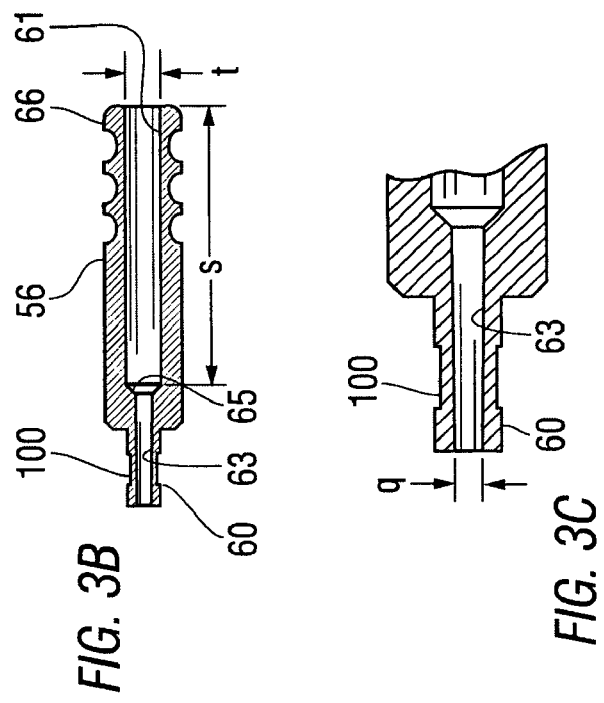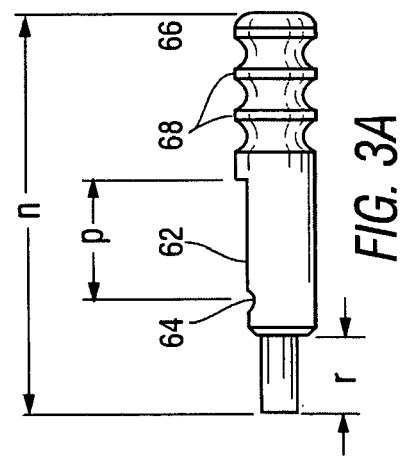

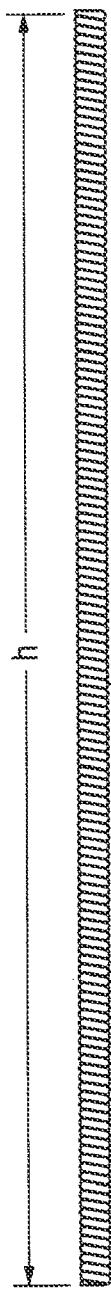
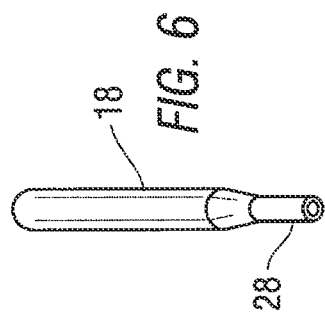
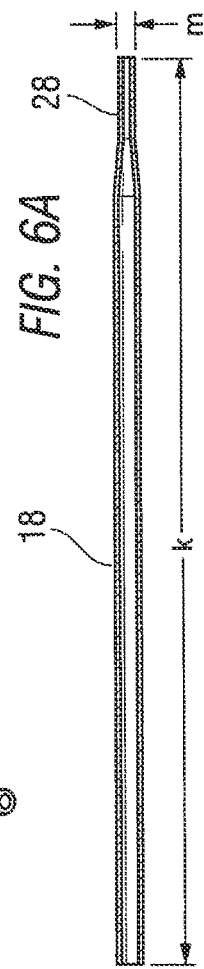
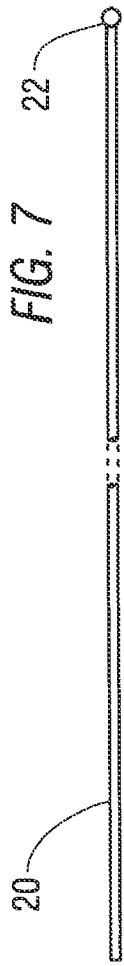
FIG. 5
FIG. 6
FIG. 6A
FIG. 7

DISPOSABLE BURR ATTACHMENT

RELATED APPLICATIONS

This application claims priority to U.S. application Ser. No. 15/911,796, filed Mar. 5, 2018, entitled "DISPOSABLE BURR ATTACHMENT" (issued as U.S. Pat. No. 10,842, 508), which is a continuation of U.S. patent application Ser. No. 14/490,079, filed Sep. 18, 2014, entitled "DISPOSABLE BURR ATTACHMENT," (issued as U.S. Pat. No. 9,907,559), which is a continuation of U.S. patent application Ser. No. 12/387,828, filed May 8, 2009, entitled "DISPOSABLE BURR ATTACHMENT" (issued as U.S. Pat. No. 8,870,873), the disclosures of which are incorporated herein by reference in its entirety. This invention relates to U.S. patent application Ser. No. 12/387,838, filed on May 8, 2009, "SURGICAL DRILL WITH CURVED BURR ATTACHMENT AND METHOD" (issued as U.S. Pat. No. 8,939,979), incorporated herein by reference in its entirety.

FEDERALLY SPONSORED RESEARCH OR DEVELOPMENT

Not applicable

TECHNICAL FIELD

This invention relates to a surgical cutting instrument (Curved Burr Attachment) and particularly to a portable and disposable burr attachment capable of use with the Curved Burr Attachment. The burr attachment of this invention has the ability to utilize different sized ball cutters primarily used for cutting bone and being capable of changing the angle of the attachment to different angles to fit into minute curved portions of the anatomy, as for example, the middle ear, although this surgical drill can be utilized for other surgical procedures.

BACKGROUND OF THE INVENTION

This invention is particularly efficacious because it is disposable and bendable without kinking and is characterized as being easily fitted into and removable from the adapter of a Curved Burr Attachment and that it is cost effective. What is meant by disposable in the context of this patent application is that the attachment, namely, the burr and its supporting structure (burr attachment) are detachable from the drill motor and the adapter and can be discarded. In the prior art, for example, the burr and its extensions are made integral with the adapter (sometimes referred to as the clutch or clutching mechanism) so that in order to make the burr disposable, the adapter, being attached thereto, is, of necessity, also disposable. It is readily understood that this is a less desirable scenario because it is less cost effective.

A good example of the differences between a more cost effective disposable component and a less cost effective disposable component is a comparison with the present invention and the instruments disclosed in the US Publication No. 2005/0177168 invented by Brunett, et al and entitled HIGH SPEED SURGICAL CUTTING INSTRUMENT (which is incorporated in its entirety herein by reference). In the present invention the comparable medical instrument is comprised of a motor, an adapter and the Curved Burr Attachment which is essentially the same elements of the instrument disclosed in the Publication, although the terminology is different. The elements in the instrument disclosed in the Publication, supra, that compares to the Curved Burr Attachment is the wire and the cutter extending at the end of the wire and its support structure, the chuck mechanism and the motor. Since the wire/cutter and support mechanism also includes an integral chuck mechanism (comparable to the adapter of the present invention) that serves to connect to the motor, the disposable portion includes the wire/cutter and its support mechanism, as well as the clutch mechanism. In contrast, the present invention merely disposes the burr attachment of the Curved Burr Attachment instrument and hence, the remaining portion of the instrument, namely, the adapter (the more expensive portions of the tool), are re-usable. What the industry needs and desires is a tool, of this type, which is extremely small, (ball cutters range in 0.5 mm-2 mm) which includes a disposable burr that is substantially inexpensive and hence, cost effective.

In addition to the ability to bend the burr attachment at-will and the burr attachment being disposable in a cost effective manner, the particular manner in which lubrication is applied to the burr is unique. In the present invention the wire-shaft of the burr is surrounded by a coil wire that extends to approximately from the proximate end to the distal end of the wire-shaft and is oriented in such a manner that the helix formed by the coil wire is in a upward direction so that by placing grease at the distal end, the rotation of the wire-shaft causes the grease to migrate from the distal end to the proximate end, namely, in the upward direction.

In addition to the lubrication feature and the bending without the kinking feature of the present invention, the coil wire which is fixed and non-rotatable, also serves another function, i.e. it dissipates heat. This is accomplished by judiciously locating the coil wire between the inner wall of the support sleeve or tube of the burr attachment and the wire-shaft such that the outer and inner edges of each coil touches both the side of the inner wall of the support sleeve and the outer periphery of the wire-shaft, respectively. This serves to conduct the heat away from the wire-shaft and from internally of the support sleeve. Distributing the heat dissipation load in this manner reduces the heat or slows down the heat at the cutter resulting in additional time that the Curved Burr Attachment can be in continuous use in a medical procedure. As one in this technology knows the heat generated by the cutter can adversely affect nerves and other portions of the anatomy. Further this arrangement attenuates vibrations created by the rotation of the wire shaft.

Another function of the coil wire is that it permits the bending of the burr attachment without causing kinking. In accordance with this invention, the burr attachment t may be bent at the factory and, at the option of the surgeon; it may be bent at-will.

SUMMARY OF THE INVENTION

An object of this invention is to provide an improved disposable burr attachment.

A feature of this invention is to provide a coil wire mounted in a support tube that surrounds the wire-shaft of the burr attachment such that it prevents kinking when the burr attachment is bent and it serves to provide heat transfer from the wire shaft to the inner diameter of the support tube surrounding the coil wire and provides a means for migrating grease from the distal end of the support tube upwardly toward the proximal end for lubricating the wire-shaft. This arrangement also attenuates vibrations created by the rotation of the coil wire.

Another feature of this invention is the inclusion of the proximal end support and the distal end support mounted on the end of the support tube that includes judicious dimensions that allow the attachment and the detachment of the burr attachment from the surgical instrument that provide means for rotating the wire shaft and locating the cutter in an exact and predetermined position.

Another feature of this invention is that it is designed to be disposable after a single use and is capable of use with a surgical drill that rotates at 80,000 revolutions per minute or higher.

The foregoing and other features of the present invention will become more apparent from the following description and accompanying drawings.

BRIEF DESCRIPTION OF THE DRAWINGS

FIG. 1 is a view in elevation and phantom illustrating a Curved Burr Attachment including the burr attachment of this invention attached thereto and illustrating the various positions that the instrument can be bent into;

FIG. 2 is a side elevation view of the burr attachment of the present invention;

FIG. 2A is a sectional view in elevation of the burr attachment depicted in FIG. 2.

FIG. 2B is a fragmentary enlarged view of a portion of FIG. 2A depicting the relationship of the wire shaft, the support tube and the coil wire of the present invention;

FIG. 3 is a perspective view of the distal end support of the present invention;

FIG. 3A is a side view in elevation illustrating the distal end support of the unit depicted in FIG. 3;

FIG. 3B is a sectional view of the distal end support depicted in FIG. 3;

FIG. 3C is an enlarged partial view of the distal end support including an annular groove formed on the peripheral surface of the smaller end portion formed in accordance with this invention;

FIG. 5 is an enlarged view in elevation illustrating the coil wire of this invention;

FIG. 6 is a perspective view illustrating the support tube for the burr attachment;

FIG. 6A is a sectional view of the support tube depicted in FIG. 6; and

FIG. 7 is a view in elevation of the wire shaft and cutter of this invention.

DETAILED DESCRIPTION OF THE INVENTION

Figure 4A:
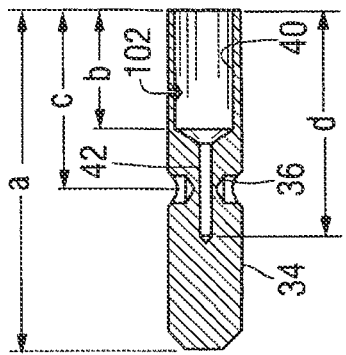
FIG. 4A is a sectional view of the proximal end support depicted in FIG. 4.

It will be noted that in the description of the elements of this invention as shown in each of the Figs. in this patent application may be out of proportion with respect to the overall picture of the inventive unit. As for example, some of the elements are shown in a small size and some of the elements are shown in an enlarged size. The purpose, obviously, is to more clearly define the invention and better describe the function of each of the elements. It is to be understood by those skilled in this art that the drawings are not manufacturing drawings, but are drawings used to illustrate the invention and to teach the concept and the workings thereof. Moreover, while the burr attachment of this invention is disclosed as being capable of use in a particular adapter, it is to be understood that other adapters can be used without departing from the scope of this invention and that this invention, amongst other things, teaches the concept of making the burr attachment, per se, disposable and bendable without incurring kinks.

As best seen in FIGS. 1 and 2, this invention is capable of use with a high speed (80,000 Io RPM −90,000 RPM) surgical instrument that is particularly efficacious for operating on small bones as for example, those found in the ear, nose and throat area, although not restricted thereto and generally illustrated as reference numeral 10 comprising a motor 12 (shown in phantom), an adapter 14 and the burr attachment 16 with the capability of being bent as shown in phantom and the burr attachment being disposable as will be described in detail herein below. While the particular motor used to rotate the drilling burr is of no moment, the X-Max® series or the E-Max® series, pneumatic and electric motors, respectively, are contemplated for use with this invention and are commercially available from the assignee of this invention, namely, The Anspach Effort, Inc of Palm Beach Gardens, Florida 33410.

The adapter 14, while not a part of this invention, is described in the aforementioned patent application bearing Ser. No. 12/387,838 and for further details reference should be made to this document. Suffice it to say that the adapter is removably coupled to the motor and the burr attachment is removably coupled to the adapter for imparting rotary motion to the cutter that is attached to the wire shaft of the burr attachment.

The invention is best described by referring to all of the Figs wherein the medical instrument sometimes referred to as the Curved Burr Attachment generally indicated by reference numeral 10 comprising the motor 12 (shown in phantom, the adapter 14 and the burr attachment 16, which is the subject matter of this invention. The burr attachment 16 is removably coupled to the adapter 14 as described in the aforementioned application bearing Ser. No. 12/387,828 and comprises a support tube 18, a wire shaft 20 and cutter 22, a distal end support 24, a proximal end support 26 (see FIGS. 2 & 3), coil wire 30, and nose cap 28. The cutter 22 may be a spherical ball with a diamond coating or with cut-in flutes. These devices are well known and for this particular medical instrument these cutters are particularly small, say from 0.5 mm to 2 mm.

All the elements of the burr attachment are made from a surgical steel or other suitable material where the hardness and tensile strength of the wire shaft 20 and attached cutter 22, the tube 18, proximal end support 26, distal end support 24 and nose cap 28 are higher than the hardness and tensile strength of the coil wire 30. (Unlike a spring, the coil wire 30 does not exhibit any spring-like characteristics and has no spring rate) These parameters are selected to assure that the burr attachment is sufficiently rigid to support the high rotational speed, yet the coil wire 30 is sufficiently malleable so that the burr attachment can be hand bent without incurring any kinking.

Figure 4C:
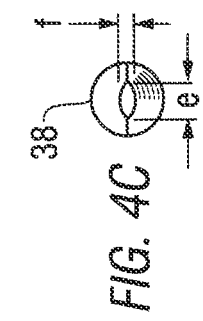
FIG. 4C is an end view of the unit depicted in FIG. 4.
Figure 4D:
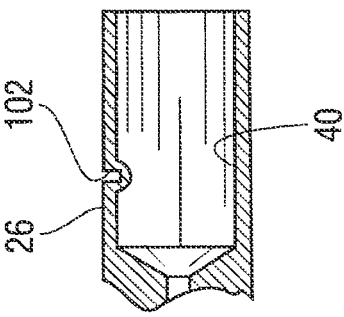
FIG. 4D is an enlarged partial view of the proximal end support illustrating An indent to be formed on the peripheral surface of the smaller end portion in accordance with this invention.
Figure 4:
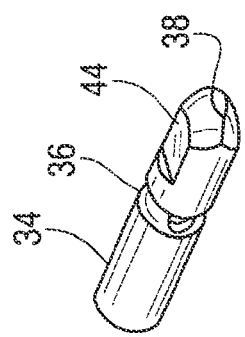
FIG. 4 is a perspective view of the proximal end support of this invention.
Figure 4B:
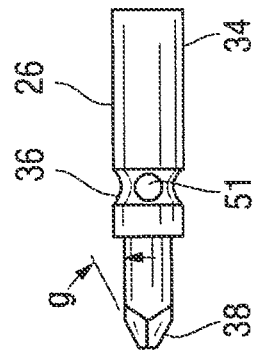
FIG. 4B is a side elevation view of the proximal end support depicted in FIG. 4.

As alluded to in the above paragraphs, the burr attachment 16 is disposable. Hence, this invention assures that the burr attachment 16 is both easily inserted into and easily removed from the adapter. To this end the distal end support 24 and proximal end support 26 are judiciously dimensioned. As best seen in FIGS. 3, 3A 3B, 4A, 4B and 4C, the proximal end support 26 includes a generally cylindrical shaped main body 34, an annular groove 36 disposed intermediate the ends thereof, a tip portion 38, a flat portion 44 formed on the periphery of the main body 34 and adjacent to the tip portion 38, large diameter recess 40 formed on one end remote from the tip portion 38 and a smaller diameter bore 42 extending axially from the large diameter recess 40. Preferably the tip portion 38 is asymmetrically shaped so that the tip is formed in a shape of an ellipse as shown in FIG. 4C. The larger diameter recess 40 serves to receive the proximal end of the distal end support 24 as will be described in more detail herein below. The smaller diameter bore 42 serves to receive the proximal end of the wire shaft 20 which is united to the proximal end support 26, say, by swaging, shrink fitting or the like. In this particular embodiment, the holes 51 serve to receive a tool (not shown) used to swage the main body 34 to wire shaft 20 to form an integral unit so that the wire shaft 20 rotates with the proximal end support 26 for powering the cutter 22. The annular groove 36 serves to cooperate with the adapter such that it couples the burr attachment so that the proximal end support 26 and wire shaft 20 are rotated. The pertinent dimensions of the proximal end support 26 are as follows in inches:

a=0.450; b 0.160; c=0.235; d=0.300; e=0.051; f=0.20; i=0.020 and the tip angle g=30°

The distal end support 24, as best seen in FIGS. 3, 3A and 3B, comprises a generally cylindrical main body 56 including a larger diameter portion 58, a smaller diameter portion 60, a flat portion 62 formed on the periphery of the main body 56 intermediate the ends thereof, a slot 64 formed on the periphery of the main body 56 adjacent to a flat portion 62 formed on the periphery of the main body 56, a larger diameter recess 61, a smaller diameter bore 63 and a grip portion 66 formed on the end of the main body 56 remote from the smaller diameter portion 60. The slot 64 cooperates with the adapter such that it locates the cutter relative to the tip of the adapter and the distal end support is held fixed relative to the adapter. The grip portion 66 in this embodiment is formed by axially spaced annular ribs but other known configurations, like knurling, can be employed. The pertinent dimensions of the distal end support 24 are substantially as follows in inches:

n=0.785; p=0.276; r=0.150; s=0.550; t=0.0725 and q=0.026

As noted in FIG. 2, the proximal end support 26 is fitted into the distal end support 24 such that the smaller diameter 60 fits into the slot 40 and the proximal end of the support tube 18 and coil wire 30 fits into the larger diameter recess 61, which define a seat 65 therefore. The diameter of the bore 63 (0.026) is larger than the diameter of the of the wire shaft 20 (0.020) such that it is capable of freely rotate therein and since the wire shaft 20 is locked into the proximal end support 26 it will rotate when the adapter rotates the proximal end support 26. The wire shaft 20 and cutter 22 are shown in FIG. 7.

As noted from FIG. 2A the coil wire 30 is mounted in the seat 80 defined by the proximal end of the nose cap 28 and the seat 65 defined by the proximal end of the recess 61 and is held in place between these seats. When the coil wire 30 is installed into the tube 18 each end thereof bears against the spring seat 65 and the spring seat 80 formed when the nose cap 28 is inserted, such that the nose cap 28 will hold the coil wire 30 in place. This assures that coil wire 30, surrounding the rotating wire shaft 20, remains fixed. An enlarged view of the coil wire is shown in FIG. 5 where the value of h=2.240. A view of the support tube 18 is disclosed in FIGS. 6 and 6A where the substantial value of k 2.650 and m=0.042.

It will also be noted and in accordance with this invention that the helix orientation of the coils of coil wire 30 are in a direction as seen in FIG. 2B are from right to left or looking from the night hand end of FIG. 2B they are in a clockwise direction. The direction of the helix serves to flow grease in the upward direction toward the proximal end. Because of the orientation of the coils, grease inserted at the distal end of the burr attachment unit in a clearance between the wire shaft 20 and inner diameter of the nose cap 22 into the tube 18 so that when the wire shaft 20 rotates this motion forces the grease toward the proximal end of the burr attachment which lubricates the entire the wire shaft 20.

It will also be noted and in accordance with this invention, as evidenced in FIG. 2B, that the peripheral top and bottom surfaces 82 and 84 of each coil of coil wire 30 touch, by a point contact, the inner diameter surface 86 of tube support 18 and the outer surface 88 of wire shaft 20 and this connection serves to minimize the heat transfer through the coil wire 30 and tube 18. This minimizing of the heat transfer of wire shaft 20 serves to keep the outer tube 18 cooler than it would otherwise be without this feature. The importance of maintaining the outer surface of tube 18 cooler by virtue of this heat transfer feature of this invention results in enhancing the operational time of the Curved Burr Attachment. In addition, because of the location of the coil wire 30, namely, by the touching of the wire shaft 20 and of the inner surface of tube 18, vibration generated by the rotating wire shaft 20 of the Curved Burr Attachment is attenuated.

It will be appreciated that in certain operations, particularly affecting the ear, the surgeon may have to re-adjust the angle of the burr attachment. Since the coil wire 30 is mounted between tube 28 and wire shaft 20, the surgeon can bend the burr attachment to any desired angle to suit the particular operation being performed. Because of this design, the burr attachment 16 will not kink and will leave a smooth bend and yet the tube and wire shaft will provide sufficient rigidity to perform the rotation in a precise manner.

In some of the embodiments of this invention the diameter of cutter 22 is smaller than the diameter of the wire shaft 20 which could under certain circumstances cause a problem, as for example, in the insertion and removal of the burr attachment 16. To solve this problem the distal end support 24 includes the annular groove 100 formed on the smaller diameter portion 60. And a dimple or indent 102 is formed on the larger diameter portion 34 adjacent to the larger bore portion 40 of the proximal end support 26, obviating the possibility of the cutter 22 and wire shaft 20 from inadvertently falling out. Obviously, the dimple or indent 102 is formed after the proximal end support 26 and the distal end support 24 are assembled in the assembled burr attachment 16.

Although this invention has been shown and described with respect to detailed embodiments thereof, it will be appreciated and understood by those skilled in the art that various changes in form and detail thereof may be made without departing from the spirit and scope of the disclosed invention.

We claim:

1. A burr attachment comprising:
   an elongated tube;
   a wire shaft supported in said elongated tube;

a coil wire mounted between an inner surface of said elongated tube and said wire shaft and surrounding said wire shaft;

a proximal end support including a single body that receives a proximal end of said wire shaft and is rotatable therewith;

a distal end support received within the single body of the proximal end support, the wire shaft extending through and rotatable with respect to a central opening extending through the distal end support, the central opening including a larger diameter bore defining a seat at a proximal end of the larger diameter bore, where a proximal end of the elongated tube abuts the seat; and, a cutter attached to said wire shaft and extending a precise distance from an end of said elongated tube, wherein said burr attachment is disposable and bendable so as to bend an axis of rotation without forming kinks therein, and wherein said coil wire is helically wound and each coil of said coil wire touches said inner surface of said elongated tube and an outer surface of said wire shaft for minimizing heat transfer from said wire shaft to said elongated tube.

2. A burr attachment as claimed in claim 1, wherein the proximal end support is rotatable relative to said distal end support.

3. A burr attachment as claimed in claim 2, wherein said proximal end support has:
a main body defined by the single body, the main body having a generally cylindrical shape, the main body adjacent a first end of the proximal end support,
a tip portion defined by the single body and disposed opposite the main body adjacent a second end of the proximal end support,
an annular groove formed intermediate the first and second ends of the proximal end support between the main body and the tip portion, and
a flat formed on the tip portion such that said proximal end support is capable of being inserted into a chuck driven by a motor for imparting rotary motion thereto.

4. A burr attachment as claimed in claim 3, wherein said single body of said proximal end support defines a large diameter bore extending from the first end of the proximal end support along said main body and a small diameter bore extending axially from said large diameter bore,
wherein said large diameter bore receives said distal end support and said small diameter bore receives said wire shaft.

5. A burr attachment as claimed in claim 3, wherein said distal end support includes:
a distal end support main body having a generally cylindrical shape, an outer surface of said distal end support main body including:
a larger diameter portion extending from a first end of the distal end support main body toward the reduced diameter portion,
a reduced diameter portion formed adjacent a second end of said distal end support main body,
a flat formed on the larger diameter portion of the distal end support main body, and a slot formed on the flat adjacent to the reduced diameter portion of the distal end support main body, and
a grip portion formed on the larger diameter portion of the distal end support main body, wherein said grip portion serves to assist in removal of said burr attachment.

6. A burr attachment as claimed in claim 5, wherein the central opening of the distal end support includes a smaller diameter bore extending axially from said larger diameter bore of said distal end support, the smaller diameter bore defining a passageway receiving said wire shaft.

7. A burr attachment as claimed in claim 6, further including:
an annular groove formed on the reduced diameter portion of said outer surface of the distal end support main body, and
a dimple formed on the main body of said proximal end support, wherein said dimple is formed after said distal end support is assembled to said proximal end support.

8. A burr attachment comprising:
an elongated tube;
a wire shaft supported in said elongated tube;
a cutter attached to said wire shaft and extending a precise distance from an end of said elongated tube;
a coil wire mounted between an inner surface of said elongated tube and said wire shaft and surrounding said wire shaft;
a proximal end support disposed at a proximal end of said wire shaft, said proximal end support receiving said wire shaft and rotatable therewith, said proximal end support including:
a main body having a generally cylindrical shape, the main body adjacent a first end of the proximal end support;
a tip portion formed opposite the main body adjacent a second end of the proximal end support;
an annular groove formed intermediate the first and second ends of the proximal end support between the main body and the tip portion; and
a flat formed on the tip portion such that said proximal end support is capable of being inserted into a chuck driven by a motor for imparting rotary motion thereto; and
a distal end support received within the proximal end support, said distal end support including:
a distal end support main body having a generally cylindrical shape, an outer surface of said distal end support main body including:
a larger diameter portion extending from a first end of the distal end support main body toward the reduced diameter portion; and
a reduced diameter portion formed adjacent a second end of said distal end support main body;
a flat formed on the larger diameter portion of the distal end support main body, and a slot formed on the flat adjacent to the reduced diameter portion of the distal end support main body,
wherein the wire shaft extends through and is rotatable with respect to a central opening extending through the distal end support, the central opening including a larger diameter bore defining a seat at a proximal end of the larger diameter bore, where a proximal end of the elongated tube abuts the seat;
wherein said proximal end support is rotary relative to said distal end support,
wherein said burr attachment is capable of being removably attached to a chuck.

9. A burr attachment as claimed in claim 8, wherein said burr attachment is disposable and bendable without forming kinks therein and includes a grip portion formed on the larger diameter portion of the distal end support main body.

10. A burr attachment adapted to be supported in a chuck having rotary motion, said burr attachment comprising:
an elongated tube;
a wire shaft supported in said elongated tube;

a fixed coil wire mounted between an inner surface of said elongated tube and said wire shaft and surrounding said wire shaft;

a proximal end support disposed at a proximal end of said wire shaft, said proximal end support receiving said wire shaft and rotatable therewith; and a distal end support received within the proximal end support, the wire shaft extending through and rotatable with respect to a central opening extending through of the distal end support, the central opening including a larger diameter bore defining a seat at a proximal end of the larger diameter bore, where a proximal end of the elongated tube abuts the seat, said distal end support being rotatable relative to said proximal end support, an outer surface of the distal end support including:

a reduced diameter portion;

a large diameter portion;

a flat formed on a periphery of said large diameter portion; and a slot formed on the flat and extending along said flat.

11. A burr attachment as claimed in claim 10, wherein said proximal end support includes a main body having a generally cylindrical shape and including an annular groove formed thereon.

12. A burr attachment as claimed in claim 11, wherein said main body of said proximal end support includes a tapered tip end.

13. A burr attachment as claimed in claim 12, further comprising:

a cutter attached to one end of said wire shaft and extending a precise distance from an end of said elongated tube;

wherein said wire shaft includes an outer surface, wherein a peripheral edge of each coil of said fixed coil wire substantially abuts said inner surface of the elongated tube and said outer surface of the wire shaft.

14. A burr attachment as claimed in claim 13, wherein said proximal end support includes a central bore extending partially through said proximal end support, said central bore having a large diameter portion and a small diameter portion.

15. A burr attachment as claimed in claim 14, wherein said central opening is a central through bore.

16. A burr attachment as claimed in claim 11, including:

another annular groove formed on the reduced diameter portion of said distal end support; and a dimple formed on main body of said proximal end support, wherein said dimple is formed after said distal end support is assembled to said proximal end support.

17. A burr attachment as claimed in claim 10, including a grip portion formed on one end of said distal end support.

18. A burr attachment comprising:

an elongated tube;

a wire shaft supported in said elongated tube;

a coil wire mounted between an inner surface of said elongated tube and said wire shaft and surrounding said wire shaft;

a proximal end support including a single body that receives a proximal end of said wire shaft and is rotatable therewith, and a distal end support received within the single body of the proximal end support, the wire shaft extending through and rotatable with respect to a central opening extending through the distal end support, the central opening including a larger diameter bore defining a seat at a proximal end of the larger diameter bore, where a proximal end of the elongated tube abuts the seat, wherein said burr attachment is disposable and bendable so as to bend an axis of rotation without forming kinks therein, wherein the elongated tube includes a central opening extending therethrough, the central opening of the elongated tube including a main diameter portion and a narrowed diameter portion along a distal end portion of the central opening of the elongated tube, and wherein the coil wire is mounted within the central opening of the elongated tube between the narrowed diameter portion of the central opening of the elongated tube and the seat defined at the proximal end of the larger diameter bore of the distal end support.

19. A burr attachment as claimed in claim 18, wherein the central opening of the distal end support includes a smaller diameter bore extending axially from the larger diameter bore of the distal end support, where the larger diameter bore of the distal end support has a diameter greater than a diameter of the smaller diameter bore of the distal end support, wherein the seat defined at the proximal end of the larger diameter bore of the distal end support includes a tapered surface, the tapered surface of the seat extending in a direction transverse to a longitudinal axis of the distal end support, wherein the elongated tube includes a tube seat defining a tapered surface extending between the main diameter portion of the central opening of the elongated tube and the narrowed diameter portion of the central opening of the elongated tube, the tube seat extending in a direction transverse to a longitudinal axis of the elongated tube, wherein a proximal end of the coil wire bears against the seat defined at the proximal end of the larger diameter bore of the distal end support, and a distal end of the coil wire bears against the tube seat.

* * * * *